United States Patent [19]

Mehra et al.

[11] Patent Number: 5,326,572
[45] Date of Patent: Jul. 5, 1994

[54] FREEZE-DRIED POLYMER DISPERSIONS AND THE USE THEREOF IN PREPARING SUSTAINED-RELEASE PHARMACEUTICAL COMPOSITIONS

[75] Inventors: Dev K. Mehra, Furlong, Pa.; Chimanlal I. Patel, Edison; Clayton I. Bridges, Jr., Somerset, both of N.J.

[73] Assignee: FMC Corporation, Philadelphia, Pa.

[21] Appl. No.: 489,166

[22] Filed: Mar. 5, 1990

Related U.S. Application Data

[63] Continuation-in-part of Ser. No. 327,934, Mar. 23, 1989, abandoned.

[51] Int. Cl.⁵ ............................................. A61K 9/14
[52] U.S. Cl. ................................. 424/484; 424/461; 424/462; 424/464; 424/465; 424/469; 424/470; 424/480; 424/481; 424/482; 424/485; 424/489; 424/486; 424/495; 514/937
[58] Field of Search ............... 424/480, 484, 486, 464, 424/465, 469, 470, 485, 489; 514/937

[56] References Cited

U.S. PATENT DOCUMENTS

| | | | |
|---|---|---|---|
| 2,800,463 | 7/1957 | Morrison | 523/309 |
| 3,942,261 | 3/1976 | Hirata et al. | 34/5 |
| 4,330,338 | 5/1982 | Banker | 424/480 |
| 4,652,442 | 3/1987 | Hopfgartner et al. | 424/495 |

*Primary Examiner*—Thurman K. Page
*Assistant Examiner*—James M. Spear
*Attorney, Agent, or Firm*—Robert D. Jackson; Patrick C. Baker

[57] ABSTRACT

Freeze-dried polymer latices, which can be reconstituted in water to give aqueous polymer dispersions having high polymer solids content, are described. The reconstituted polymer dispersions are useful in preparing sustained-release drug formulations, particularly of water-soluble drugs, by the wet granulation method without over wetting.

8 Claims, No Drawings

FREEZE-DRIED POLYMER DISPERSIONS AND THE USE THEREOF IN PREPARING SUSTAINED-RELEASE PHARMACEUTICAL COMPOSITIONS

This is a continuation-in-part of U.S. application Ser. No. 327,934, filed Mar. 23, 1989, now abandoned.

TECHNICAL FIELD

This invention relates to polymer dispersions, particularly aqueous polymer dispersions produced by redispersion of freeze-dried precursor aqueous polymer dispersions. The invention is also concerned with the use of such polymer materials for preparing sustained-release pharmaceutical compositions.

BACKGROUND OF THE INVENTION

It is well known to produce solid oral dosage forms of a type commonly referred to as sustained-release systems in which a pharmacologically active ingredient contained therein is released in a controlled manner in order to elicit the desired biological response. For instance, such formulations are used to provide delayed action of a drug for an interval of time or until it encounters certain physiological conditions. An example of the latter is a medication which is resistant to the acidic gastric juices but breaks down in the alkaline environment of the intestines with concomitant release of the active component.

Sustained-release properties of orally administered pharmaceutical compositions can be attained by means of diffusional systems in which the release rate of a drug is governed by its migration through a polymer membrane. There are two techniques whereby this can be effected. In one of these, a core of drug is encapsulated by a polymeric membrane. In the other technique and the one with which the invention is particularly concerned, the drug components are uniformly distributed throughout an inert polymeric matrix.

In preparing the matrix type of solid dosage forms, for example, granules, pellets and tablets, the wet granulation method is widely employed. The steps included are (1) weighing, (2) mixing, (2a) sieving, (2b) mixing, (3) granulation, (4) wet screening, (5) drying, (6) dry screening, (6a) addition of other desired ingredients, (7) lubrication and if tablets are desired, and (8) compression. Granules of the matrix containing drug are produced by wetting the powdered mass with a solution/suspension of the polymer followed by screening and drying of the wet granulation. After the drying step, the granulation is screened to the desired particle size.

The matrix containing a predetermined amount of polymer can be formed by adding to the dried powdered ingredients, a specific volume of a solution of the polymer in an organic solvent. A variation in such matrix formation, utilizes the polymer in the form of an aqueous dispersion. When carrying out the granulation, mixing of the liquid and solid component must be carefully controlled. The general rule of thumb is to add the liquid to the powdered mass until it takes on the consistency of damp snow or brown sugar. If the liquid component is an aqueous polymer dispersion, over wetting of the powdered mass may occur while attempting to deposit the desired weight of polymer. This will result in difficulties in the further processing of the over wetted granulation. On the other hand, insufficient wetting produces granules that are too soft, and generates excessive quantities of fines. This results in poor drug distribution and unsatisfactory flow and compression properties.

The trend to water based polymer systems is receiving increased attention owing to the implementation in recent years of stronger government safety regulations limiting solvent emissions from commercial chemical operations. The usual hazards, that is, toxicity and flammability are also associated with solvent use.

A class of aqueous polymer dispersions that are highly suitable in formulating pharmaceutical products are those in which the polymer particles are formed of at least one water-insoluble polymer of the type disclosed in U.S. Pat. No. 4,330,338 to Gilbert S. Banker. The aqueous polymer dispersions described therein are pseudolatices produced by dissolving the polymer in a water-immiscible solvent, forming an emulsion of the solvent solution in water and removing the water leaving very small particles of the polymer in the aqueous vehicle. Surfactants can be employed to facilitate emulsion formation.

The aqueous polymer dispersions of the cited patent were developed as coatings for solid pharmaceutical dosages and to this end were admixed with selected additives. These included annealing agents in the form of water-soluble polymers; emulsion stabilizers, particularly cetyl alcohol and n-decane; polishing agents, release agents, etc.

The water-insoluble polymer in the Banker aqueous dispersions can be of various types as exemplified by chemically modified, solvent soluble cellulose derivatives such as cellulose ethers and esters illustrative members of which are ethylcellulose and cellulose acetate phthalate. Other water-insoluble polymers may be used alone or added to the cellulosic polymer.

Although having wide application in formulating coating materials, the aqueous polymer dispersions of Banker are not readily amenable to the manufacture of pharmaceuticals by the wet granulation method. The main problem in this regard, is producing the Banker dispersions with sufficient polymer levels to provide matrix formation for sustained release without causing over wetting. Simply increasing the amount of polymer solvent solution to be emulsified in forming the pseudolatices is ineffective due to excessively high viscosities. Another possible approach is to use a more concentrated polymer solvent solution but this tends to promote formation of large polymer particles or clumps instead of a stable dispersion. Nor does raising polymer levels by removing some of the aqueous phase provide the answer since it leads to excessive foaming and unstable dispersions. Because of these deleterious effects, it is difficult to prepare Banker's dispersions in which the polymer content is much above about 30% by weight. At this level of polymer content, attendant over wetting would be a problem, particularly where the sustained-release composition produced from the dispersions contains a water-soluble drug substance and where the high ratio of the polymer to soluble drug is intended.

SUMMARY OF THE INVENTION

It has now been discovered that the drawbacks aforesaid can be overcome and polymer dispersions of the type described in the Banker patent obtained which are suitable for producing sustained-release matrix systems for active agents such as drugs, medicinals and the like.

These findings are implemented in accordance with the invention by first subjecting the Banker polymer dispersion to freeze drying whereby they are converted into solid materials, usually of a powdery consistency. Such is the nature of the freeze-dried dispersions that they can be reconstituted in water to give aqueous polymer dispersions having a wide range of polymer content. Highly concentrated polymer dispersions can be produced, suitable for preparing controlled release pharmaceutical compositions by the wet granulation method.

DETAILED DESCRIPTION

Freeze drying of the starting polymer dispersion is carried out generally in the known manner. Typically, a dispersion containing about 30% w/w polymer solids such as ethylcellulose is placed in trays and exposed to freezing temperatures. The frozen solids are removed, crushed into small pieces and returned to the freezer trays for drying. The freeze-drying system is evacuated and the temperature lowered to −22° C. to 2° C. Controlled heat of about 38° C. is applied to the freezer shelves during the drying cycle. Processing temperatures may vary somewhat to accommodate different polymers. Normally, a polymer should not be heated above its glass transition point lest the polymer particles becomes tacky and undergo coalescence with concomitant settling of the dispersion.

The dried dispersion is removed from the freeze drier and stored under moisture free conditions.

Aqueous polymer dispersions of the desired polymer content are prepared by stirring a mixture of the requisite amounts of freeze-dried powder and water. Preferably, the wetted powder is allowed to stand a few hours prior to agitation. The resulting suspension consists primarily of agglomerated polymer particles of various dimensions. Further, reduction in particle size can be brought about by subjecting the suspension to comminuting forces using standard devices such as colloid mills, ultrasonic vibrations, homogenizers, etc.

The present invention provides aqueous polymer dispersions in a wide choice of polymer concentrations, with upper polymer levels approaching about 70% in some instances. Such high level polymer dispersions can be made from relatively dilute precursor polymer dispersions which have been freeze dried. This has the advantage of avoiding the high viscosities and emulsion instability during emulsification of the intermediate solvent/polymer solution when preparing high solids polymer dispersions directly as taught in the Banker patent. Other advantages afforded by the freeze-dried polymer product of the invention are of particular interest to formulators and include the following:

1. Reduction in shipping charges as water is eliminated,
2. Reduction in storage space (weight and volume) as water is eliminated,
3. Means of controlling viscosity of reconstituted dispersions,
4. Flexibility in adjusting the polymer content of the reconstituted dispersions, and
5. Improved consistency of wet granulated mass for screening.

The freeze-dried polymer dispersions of the invention can be reconstituted in water to provide aqueous polymer dispersions in which high polymer levels are more readily achieved than is the case with the technique of Banker. Such dispersions are especially useful as a binder or matrix in formulating water-soluble drugs by the wet granulation method. The polymer content of the dispersion must be such that sufficient polymer is incorporated into the powdered drug formulation to serve as a binder without causing over wetting of the components. Of course, the freeze-dried polymers can be reconstituted to give a wide variety of polymer concentration to suit different formulation requirements. In preparing wet granulations with the polymer dispersions of the invention, the known procedures of the art are followed. Thus, the quantity and concentration of the polymer dispersion will be dictated by the drug release characteristics of the final dried granulated product. Other things being equal, the higher the polymer loading of the matrix the slower the release rate of the drug. Different drugs will exhibit different release rates at a given matrix loading. Those skilled in the pharmaceutical art will select the polymer dispersion which meets their formulation requirements.

The aqueous polymer dispersions of the invention may advantageously include at least one member of a water-insoluble cellulose derivative of the group previously enumerated herein. An especially preferred cellulose derivative is ethylcellulose. However, other polymers both water-insoluble and soluble type may be present with the principal polymer in order to provide different rates of drug release from the polymer matrix. Generally speaking, where the formulation contains water-soluble ingredients, the polymer mix will be composed of the water-insoluble or hydrophobic type. With water-insoluble ingredients, some of the water-soluble or hydrophilic polymers will make up the matrix.

Examples of water-soluble polymers, the purpose of which is to serve as viscosity and suspension agents, include hydroxypropyl cellulose, hydroxypropyl methylcellulose, methylcellulose, methylethylcellulose, polyvinylpyrrolidone and/or sodium carboxymethylcellulose; gums, including official gums, such as pectin acacia-USP, tragacanth-USP, as well as nonofficial gums such as karaya, locust bean, chondrus, and alginic acid derivatives, etc. Other materials of possibly desirable application, though believed to be less desirable than those first listed, include high molecular weight carboxy vinyl polymer such as Carbopol 934 polymer available from B. F. Goodrich Company, provided it is employed in amounts not above 2% or 3% concentration and is neutralized to form a soluble salt; hydroxyethylcellulose, available as Cellosize from Union Carbide Company, sodium alginate, propylene glycol ester of alginic acid, available as Kelgin and Kelcoloid respectively from the Delco Chemical Company and polyvinyl alcohol.

The polymer dispersions may require a plasticizer, examples of which are propylene glycol, glycerin, glyceryl triacetate, polyethylene glycol, dibutyl sebacate, triethyl citrate, tributyl citrate, monoglycerides, triethyl phthalate, etc.

The percentage of plasticizer will vary depending on the scope of the polymer. In the case of ethylcellulose aqueous dispersion, the plasticizer ranges from about 20% to about 35% by weight of the polymer.

Other water-insoluble polymers include maleic anhydride copolymers, including poly(methyl vinyl ether/maleic anhydride), that is, the Gantrez Series, ethylene maleic anhydride, styrene maleic anhydride, and various straight chain and branched alkyl esters of maleic anhydride copolymers, including ethyl, propyl, butyl, etc., to $C_{18}$ alkyl half esters, and butyl, isobutyl, etc., to $C_{18}$ alkyl quarter esters; acrylic/acrylate copolymers and acrylate polymers, including Eudragit E-30D a 70:30 ethylacrylate-methylmethacrylate copolymer having a preferred molecular weight of about 800,000 and Eudragit L-30D, a 50:50 methacrylic acid ethyl acrylate copolymer having a preferred molecular weight of about 250,000 and biodegradable polymers, including polylactic acid, d and l (+ and −), polylactic/polyglycolic acid copolymer, polypeptides such as glutamic acit/leucine copolymer, glycolides, -propiolactone, tetramethylglycolide, -butyrolactone, povalolactone, and cyclic esters of -hydroxybutyric acid, -hydroxyisobutyric acid, -hydroxyl methylvaleric acid, -hydroxyliquocenic acid, -phenyl lactic acid, and -hydroxy ethylbutyric acid.

It is often desirable to employ surfactants in producing the polymer dispersions of the invention. The surfactants may be anionic such as sodium lauryl sulfate (USP), cationic such as the quaternary ammonium halides (such as cetyl pyridinium chloride) or nonionic, such as linear fatty alcohol ethoxylates (exemplified by Alkasurf LA3, LA7, LA9 or LA12 available from Alkanol Chemical Ltd. of Mississauga, Ont. Canada) or the polyoxyethylene condensation products (exemplified by Spans and Tweens or polyoxyethylenepolypropylene glycol as Pluronic F68, available from Wyandotte Chemicals Corp., Wyandotte, Mich.). Other agents including materials such as polyglycerol esters of a fatty acid, polyoxyethylene sorbitan monolaurate, polyoxyethylene sorbitan tristearate, polyoxyethylene sorbitan monostearate, polyoxyethylene sorbitan monooleate, propylene glycol mono- and diesters of fats and fatty acids, sodium lauryl sulfate and sorbitan monostearate are useful to serve such functions. Generally, the emulsions and lactices of the instant invention can be formed without surfactants or emulsifiers, but in many instances, finer particle size and greater stability are attained with such additives.

Various other additives, such as beeswax, (yellow, bleached or white and white natural), candelilla wax, carnauba wax, cocoa butter, fatty acids such as those in the food additives, mono, di- and triglycerides (including glyceryl monostearate, monooleate, etc. and self-emulsifying glyceryl monostearate), glycerol-lacto stearate, oleate or palmitate (other self-emulsifying waxes), glyceryl-lacto esters of fatty acids (also self-emulsifying) lauric acid, lauryl alcohol, linoleic acid, octyl alcohol and acetate, and paraffin may be advantageously added to the latex granulation as release rate modifiers. Cetyl alcohol and n-decane are useful as emulsion stabilizers.

Any functionally active ingredient may be employed in the present invention such as a pharmaceutically active agent, a flavor, a fragrance, an insecticide, a herbicide, a veterinary product or the like. However, the invention was developed primarily as a means of formulating matrix-type, sustained-release dosage systems by the wet granulation method without over wetting.

Such granulation may then be subsequently processed into i) dry granules, ii) pellets, beads or seeds, and iii) compressed tablets or may be filled into hard or soft gelatin capsules. These solid dosage delivery devices may contain pharmacologically active compounds representing various classes viz.

Analgesics

Opiates and opioids including the purified alkaloids of opium and the synthetic compounds that resemble morphine and its various derivatives for example but not limited to 1) phenylpiperidine derivatives (meperidine, alphaprodine);
2) phenanthrene derivatives (levorphanol, butorphanol);
3) diphenylheptane derivatives (methadone, propoxyphene); and
4) benzomorphan derivative (pentazocine), etc.

Nonopiates such as salicylates (aspirin), paraaminophenol derivative (acetaminophen), anthranilic acid derivative (mefenamic acid) and phenylpropionic acid derivatives and related compounds (fenoprofen calcium, ibuprofen, naproxen).

Mixtures of analgesics and antipyretics (APC), mixtures containing codeine, mixture containing hydrocodone, mixtures containing meperidine, mixtures containing oxycodone, mixture containing pentazocine, mixtures containing propoxyphene and mixtures containing analgesics with sedatives.

Antiarthritic Antigout Drugs—Oxyphenbutazone phenylbutazone, sulindac, tolmetin sodium indomethacin, probenecid, allopurinol, colchicine.

Central Pain Syndromes—Carbamazepine, phenytoin sodium.

Antianxiety and Hypnotic Drugs—Benzodiazepines, for example, but not limited to chlorodiazepoxide, diazepam, proazepam, etc. Nonbenzodiazepines, for example, but not limited to Barbiturates—phenobarbital, pentobarbital, etc., Chloral derivatives—triclofos sodium, miscellaneous compounds, for example, ethchlorvynol, glutethimide, mebrobamate, etc.

Antipsychotic Drugs, for example, fluphenazine, haloperidol thiothixene, trifluperazine, perphenazine, prochlorperazine, trifluromazine, thioridazine, etc.

Anti-Parkinsonism—Dopamine regulators, for example, amantidine, levodopa, combination of levodopa and carbidopa.

The specific centrally active anticholinergics and antihistamines used in treating Parkinsonism, for example, trihexphenidyl, benztropine, diphenhydramine, etc.

Respiratory Tract Drugs

Antihistamines, for example, chloropheniramine maleate, diphenyldramine,

Nasal decongestants, phenylpropanolamine.HCl, pseudoephedrine.HCl,

Antitussives—guaifenesin, dextromethorphan HBr

Antiasthmatics—Theophylline, albuterol, terbutaline, isoproterenol

Cardiovascular-Renal Drugs

Vasodilators isosorbide dinitrate, hydralazine HCl, nitroglycerine, etc.

Antiarrhythmics—Quinidine derivatives, procainamide, verapamil, propranolol, etc.

Peripheral Vascular Agents—Papaverine, nicotinic acid, nylidrium, cyclandelate, etc.

Antihypertensives—Thiazide type, for example, chlorthiazide, loop type, for example, furosemide, potassium sparing, for example, spironolactone, etc.; prazosin HCl, metoprolol tartarate, etc.

Endocrine and Metabol Agents

Hydrocortisone, dexamethasone, halotestin, progesterone
Acetoheximide, chloropamide, tolbutamide
Water and electrolyte replenishers, for example KCl
Vitamins and minerals Antihyperlipidemics—Lorelco
Antiobesity—Diethylpropion, phenmetrazine.HCl Gastrointestinal Agents Cimetidine, ranitidine, famotidine,
Sulfathalidine, sulfasalazine Hematologics Ferrous fumarate, sulfate or gluconate
Folic acid, anticoagulants, etc.

Oncolytic

Chlorambucil, cyclophosphamide, methotrexate

Antimicrobial

Penicillins, cephalosporins, chloramphenicol and derivatives
Macrolide and lincosamide antibiotics (erythromycin and cleocin, respectively) tetracyclines, aminoglycosides, sulfonamides Antiparasitic Antimalarials, antiprotozoals, etc.

The invention is illustrated by the following non-limiting examples.

The Solid Freeze-Dried Polymer Dispersons

EXAMPLE 1

A stabilized pseudolatex of 30% by weight ethylcellulose in water, available from the FMC Corporation as Aquacoat ®, was freeze dried in a commercial freezer as previously described herein to give a friable white powder. A plasticized aqueous polymer dispersion containing 40% of the freeze-dried product and 10% Myvacet ® 9-40 plasticizer, an acetylated monoglyceride sold by Eastman Kodak, was prepared by homogenizing the components in the requisite amount of water for about 90 minutes. There was obtained a stable polymer dispersion having a total solids content of 50% of which 40% is ethylcellulose polymer and 10% plasticizer.

EXAMPLE 2

Following the procedure of Example 1, a pseudolatex of cellulose acetate phthalate is subjected to freeze drying.

EXAMPLE 3

Following the procedure of Example 1 is carried out using a pseudolatex of cellulose acetate propionate.

EXAMPLE 4

The procedure of Example 1 is repeated in which a pseudolatex of polyvinyl acetate phthalate is prepared.

EXAMPLE 5

The procedure of Example 1 is repeated using cellulose acetate butyrate.

The freeze-dried solid polymer solids aforesaid can be reconstituted in water to give polymer dispersions having a wide range of polymer concentrations from about 30% up to a level of about 70% by weight. The initial polymer suspension containing course particles can be homogenized in the known manner to further reduce the size of the particles.

EXAMPLE 6

A stabilized pseudolatex of 30% by weight ethylcellulose in water, available from the FMC Corporation as Aquacoat ®, was mixed with plasticizer triethyl citrate at 24% w/w concentration based on Aquacoat ® solids and 4 PMC E-5 (Methacel ®). The plasticized Aquacoat ® was freeze dried in a commercial freezer as previously described herein to give a dry powder.

EXAMPLE 7

Following the procedure of Example 6, Aquacoat ® was mixed with triethyl citrate plasticizer at 24% w/w concentration based on Aquacoat ® solids. To this blend was added a 15% by weight aqueous hydroxypropyl methylcellulose (Methacel ® E-5 sold by Dow Corporation) to give a final formulation having a ratio of Aquacoat ® solids to Methacel ® E-5 of 10 to 1. The mixture was then freeze dried as previously described to give a dry powder.

EXAMPLE 8

Following the procedure of Example 6, Aquacoat ® was mixed with 15% by weight aqueous Methacel ® E-5 to give a nonplasticized dispersion in which the ratio of Aquacoat ® solids to water-soluble polymer is 10 to 1. The mixture was then freeze dried.

EXAMPLE 9

Aquacoat ® was mixed with 15% by weight aqueous polyvinylpyrrolidone (PVP) K-30, sold as Kollidon 30 by BASF, to give a nonplasticized dispersion in which the ratio of Aquacoat ® solids to PVP is 10 to 1. The mixture was then freeze dried.

EXAMPLE 10

Following the procedure of Example 6, a dispersion of Aquacoat ® and triethyl citrate was prepared in which the concentration of the citrate ester was 24% w/w. The dispersion was then free dried.

The freeze-dried dispersions of the Examples can be reconstituted to give an aqueous dispersion of the desired solids content up to about 70% by weight.

Preparation of Active Release Composition By Wet Granulation Method

Example A, Drug: Potassium Chloride

Potassium chloride (USP powder) was granulated with two specimens of aqueous ethylcellulose dispersions in a Hobart mixer, Model N-50. One specimen was reconstituted from the freeze-dried material of Example 1 containing 50% solids of which 40% was Aquacoat ® ethylcellulose solids and 10% was plasticizer (Myvacet ® 9-40). The other specimen which served as the control was commercial Aquacoat ® containing 34.9% solids of which 7.0% was plasticizer and 27.9% Aquacoat ® solids.

Samples of each dispersion was added to the potassium chloride while carefully avoiding over wetting. After addition of each dispersion, the wet mass (consistency of damp snow) was agitated in the mixer for 5 minutes at speed setting 2. The wet mass was passed through a 14 mesh (U.S. Standard) screen and dried in an air forced oven such as the Blue M oven at 40° C. for 2 hours. Dried granules were screened through a 16 mesh screen without force.

The dried potassium chloride granules contained 7.1% and 16.7% w/w polymer solids including plasticizer made from the commercial Aquacoat ® (34.9% solids) and reconstituted freeze-dried ethylcellulose dispersion (50.0%) solids respectfully. These results are summarized below:

|  | Weight (g) | Solids (g) | Percent Solids in Final Granules (%) |
| --- | --- | --- | --- |
| Control: Commercial Aquacoat ® ECD-30 | | | |
| KCl | 250 | 250.0 | 92.9 |
| Plasticized Aquacoat ® | 55 | 19.2 | 7.1 |
| (34.9% solids) |  | 269.2 g | 100% |
| Freeze-Dried Aquacoat ® | | | |
| KCl, USP Powder | 250 | 250 | 83.3 |
| Plasticized Aquacoat ® | 100 | 50 | 16.7 |
| (50% solids) |  | 300 g | 100% |

As the above obtained results clearly show, more polymer solids can be deposited at the wet granulation stage without over wetting using the reconstituted high level polymer dispersions of the invention.

Example B, Drug: Theophylline

Theophylline was granulated with two specimens of aqueous ethylcellulose dispersions in a Hobart Mixer, Model N-50. One specimen was reconstituted from freeze-dried Aquacoat ® and contained 60.4% solids of which 45.3% was Aquacoat ® solids and 15.1% was plasticizer (Myvacet ® 9-40). The other specimen was commercial Aquacoat ® containing 34.9% solids of which 7.0% was plasticizer and 27.9% Aquacoat ® solids.

Samples of each dispersion was added to the theophylline while carefully avoiding over wetting. After addition of each dispersion, the wet mass (consisting of damp snow) was agitated in the mixer for 5 minutes at speed setting 2. The wet mass was passed through a 14 mesh (U.S. Standard) screen and dried in an air forced oven such as the Blue M oven at 40° C. for 2 hours. Dried granules were screened through a 16 mesh screen without force.

The dried theophylline granules contained 13.5% and 41.5% w/w polymer solids including plasticizer made from the commercial Aquacoat ® (34.9% solids) and reconstituted freeze-dried ethylcellulose dispersion (60.4% solids) respectfully. These results are summarized below:

|  | Weight (g) | Solids (g) | Percent Solids in Final Granules (%) |
| --- | --- | --- | --- |
| Control: Commercial Aquacoat ® CD-30 | | | |
| Theophylline | 250 | 250.0 | 86.5 |
| Plasticized Aquacoat ® | 112 | 39.1 | 13.5 |
| (34.9% solids) |  | 289.1 g | 100% |
| Freeze-Dried Aquacoat ® | | | |
| Theophylline | 250 | 250 | 58.5 |
| Plasticized Aquacoat ® | 293 | 177 | 41.5 |
| (60.4% solids) |  | 427 g | 100% |

The above obtained results clearly show that more polymer solids can be deposited at the wet granulation stage without over wetting using the reconstituted high level polymer dispersions of the invention.

As previously pointed out, the freeze-dried pseudolatices of the invention can be redispersed to provide polymer dispersions having polymer concentrations approaching about 70% by weight. This means that the reconstituted polymer dispersions can be tailored to provide without over wetting, a polymer matrix or binder having the desired release properties for pharmaceutical agents of varying water solubility.

It will be evident to those skilled in the art that changes and modifications can be made to the invention without departing from the spirit and scope thereof.

We claim:

1. A method of preparing an aqueous polymer dispersion in which the polymer concentration is from about 30% to about 70% comprising the steps of:
   (1) forming an aqueous polymer pseudolatex by dissolving a polymer in a water-immiscible solvent; emulsifying the polymer solvent solution in water at a polymer content of about 30% and removing the solvent;
   (2) freeze drying the pseudolatex from step 1; and
   (3) redispersing the freeze-dried pseudolatex in water to the desired polymer content up to about 70%.

2. The method of claim 1 in which the polymer is at least one water-insoluble polymer selected from the group consisting of ethylcellulose, polyvinyl acetate, polyvinyl acetate phthalate, cellulose acetate, cellulose acetate phthalate, and cellulose acetate butyrate.

3. The method of claim 2 in which the polymer is ethylcellulose.

4. In the method of preparing a pseudolatex by forming a solution of a polymer in a water-immiscible solvent, forming an emulsion of the solvent solution in water and removing the solvent from the emulsion, the improvement of avoiding high viscosity and/or emulsion instability when carrying out the emulsification at high polymer levels, comprising the steps of:
   (1) forming a first pseudolatex at a polymer concentration up to about 30%;
   (2) subjecting the first pseudolatex to freeze drying;
   (3) recovering the solid freeze-dried pseudolatex from step 2(b), and
   (4) redispersing the solid freeze-dried pseudolatex from 3. in water to give a pseudolatex containing polymer levels up to about 70%.

5. The method of claim 4 wherein the polymer is ethylcellulose.

6. A method of preparing a sustained-release dosage form by adding the aqueous polymer dispersion of claim 1 to powdered drug components in the known wet granulation process to form solid granules in which the drug components are distributed in a polymer matrix.

7. The method of claim 6 wherein the polymer is at least one water-insoluble polymer selected from the group consisting of ethylcellulose, polyvinyl acetate phthalate, cellulose acetate phthalate, cellulose acetate, cellulose acetate butyrate and polyvinyl acetate.

8. The method of claim 7 wherein the polymer is ethylcellulose.

* * * * *